(12) United States Patent
Chen

(10) Patent No.: US 7,687,785 B2
(45) Date of Patent: Mar. 30, 2010

(54) ULTRAVIOLET STERILIZER WITH A DOUBLE-CHAMBER STRUCTURE

(75) Inventor: Jian Chen, Fujian (CN)

(73) Assignee: Fujian Newland EnTech Co., Ltd., Fujian (CN)

( * ) Notice: Subject to any disclaimer, the term of this patent is extended or adjusted under 35 U.S.C. 154(b) by 417 days.

(21) Appl. No.: 11/600,609

(22) Filed: Nov. 16, 2006

(65) Prior Publication Data
US 2007/0125960 A1    Jun. 7, 2007

(30) Foreign Application Priority Data
Nov. 19, 2005    (CN)    ................ 2005 1 0125233

(51) Int. Cl.
*G01N 23/10* (2006.01)
(52) U.S. Cl. .................. 250/436; 250/432 R; 250/428; 250/435; 210/748; 442/24
(58) Field of Classification Search ................ 250/428, 250/432 R, 435, 436; 210/748; 422/24
See application file for complete search history.

(56) References Cited
U.S. PATENT DOCUMENTS
6,503,447 B1 *    1/2003    Mondjian et al. .............. 422/4

6,683,313 B2 *    1/2004    Chen et al. .............. 250/455.11
6,932,903 B2 *    8/2005    Chang ....................... 210/192

FOREIGN PATENT DOCUMENTS
CN    1311160 A    9/2001
WO    WO 03/095369    11/2003

* cited by examiner

*Primary Examiner*—Jack I Berman
*Assistant Examiner*—Hanway Chang
(74) *Attorney, Agent, or Firm*—Saliwanchik, Lloyd & Saliwanchik

(57) ABSTRACT

A UV sterilizer with a double-chamber structure comprises an inner tube and an outer tube with different size, the inner tube being partly surrounded by the outer tube thereby forming an inner chamber and an outer chamber, the inner chamber is the space encircled by the inner tube and the outer chamber is the annular space encircled by the overlapped portions of the inner tube and the outer tube; a first end portion of the inner tube is located outside the outer chamber and provided with a first water port, a second end portion of the inner tube is located inside the outer chamber and provided with a second water port communicating with the outer chamber; a first end portion of the outer tube is sealingly connected with the outer wall of the inner tube, while a second end portion of the outer tube is sealed; sleeved UV lamps are arranged in the outer chamber or in both the inner chamber and the outer chamber.

16 Claims, 4 Drawing Sheets

ULTRAVIOLET STERILIZER WITH A DOUBLE-CHAMBER STRUCTURE

FIELD OF THE INVENTION

The invention relates to an ultraviolet (UV) sterilizer, and more particularly to a fluid UV sterilizer with a double-chamber structure.

DESCRIPTION OF RELATED ART

Chinese patent CN 01105462.x in the name of the same applicant disclosed a composite UV sterilization device, comprising a sterilization chamber with a cylindrical shape or other shape and having a water inlet port and a water outlet port. The sterilization chamber may be formed into a casing configuration at the location(s) of one or both of the water ports, and the casing configuration consists of an outer tube and an inner tube. On the end portion of the chamber wall there are provided with apertures. One end face of the outer tube is sealingly fixed on the chamber wall, while the other end face of the outer tube is sealingly fixed to a flange mount, which is located at an end of the sterilization chamber. In order to prevent the water inside the outer tube from leaking, all the apertures at the end portion of the chamber wall should be located inside the outer tube when the outer tube is secured. A welding process may be used for sealingly fixing the outer tube. There are n (n≧1) UV lamps with glass sleeves arranged in the sterilization chamber, and the connection between the UV lamps with glass sleeves and a main positioning plate is sealed by a seal fitting for the glass sleeves, so as to prevent the water and UV light from leaking. A sealing gasket is provided between the main positioning plate and the flange mount at an end of the sterilization chamber to avoid water leakage. According to specific conditions, the water ports and the sterilization chamber may be sized for use in the sterilization of seawater, drinking water, treated wastewater and other kinds of water. However, in the above-mentioned invention, when a large volume of water is treated and the diameter of the sterilization chamber is very large, since the UV lamps are arranged in the sterilization chamber, the flow velocity at the end portion differs from the flow velocity at the medium portion of the sterilization chamber and thus turbulence will occur, such that part of the water receives less UV radiation due to its accelerated flow velocity, thereby impairing the sterilization effect. Therefore, it is desirable to provide a UV sterilization device capable of treating water in large volume, achieving an uniform flow velocity everywhere in the sterilization chamber and avoiding the occurrence of turbulence, without impairing the sterilization effect.

SUMMARY OF THE INVENTION

Therefore, the object of this invention is to provide a UV sterilization device capable of treating fluid in large volume and avoiding the occurrence of turbulence, without impairing the sterilization effect.

In order to achieve the above object, the invention provides a UV sterilizer with a double-chamber structure, wherein the UV sterilizer comprises an inner tube and an outer tube with different size, the inner tube being partly surrounded by the outer tube thereby forming an inner chamber and an outer chamber, the inner chamber being the space encircled by the inner tube and the outer chamber being the annular space encircled by the overlapped portions of the inner tube and the outer tube; at least one sleeved UV lamp is arranged in the outer chamber; a first end portion of the inner tube is located outside the outer chamber and provided with a first water port, and a second end portion of the inner tube is located inside the outer chamber and provided with a second water port communicating with the outer chamber; a first end portion of the outer tube is sealingly connected with the outer wall of the inner tube, while a second end portion of the outer tube is sealed, and a third water port is provided on the outer tube. In order to achieve a better sterilization effect, at least one water distributor having at least one through-hole is provided in the outer chamber for adjusting the water flow, and the water distributor can further be used as support member for the sleeved UV lamp(s). The water ports and the sterilization chamber may be sized according to specific conditions. When a single sterilizer is used, the third water port on the outer tube and the first water port on the inner tube, which is located outside the outer tube, are respectively used as water outlet port and water inlet port of the sterilizer, or vice versa.

Further, the invention also provides a UV sterilizer with a double-chamber structure, wherein the UV sterilizer comprises an inner tube and an outer tube with different size, the inner tube being partly surrounded by the outer tube thereby forming an inner chamber and an outer chamber, the inner chamber being the space encircled by the inner tube and the outer chamber being the annular space encircled by the overlapped portions of the inner tube and the outer tube; at least one sleeved UV lamp is arranged in the outer chamber; a first end portion of the inner tube is located outside the outer chamber and provided with a first water port, a second end portion of the inner tube is located outside the outer chamber and sealed, and a second water port communicating with the outer chamber is provided on part of the wall of the inner tube, which part being located inside the outer chamber; both the first end portion and the second end portion of the outer tube are sealingly connected with the outer wall of the inner tube, and a third water port is provided on the outer tube.

Preferably, a plurality of UV lamps are used in a sterilizer.

The UV lamps may be provided on the sterilizer in the following manners:

1. One end portion of the outer tube is sealed by a mounting plate for the sleeved UV lamps; at least one mounting hole is provided in the mounting plate for mounting the sleeved UV lamps, such that sleeved UV lamps are arranged in the outer chamber; the connection between the mounting plate and the sleeved UV lamps is sealed to prevent water leakage.

2. The sleeved UV lamps may be mounted on the end face of the outer tube, which face is sealingly connected with the inner tube; or alternatively, the sleeved UV lamps may be mounted on a sealing cover, which sealingly connects the outer tube with the outer wall of the inner tube.

3. The sleeved UV lamps may be provided simultaneously on both end portions of the outer chamber.

4. The sleeved UV lamps may be mounted on the wall of the outer tube.

5. It is also possible to provide sleeved UV lamps in the inner chamber, so as to enhance the sterilization effect.

The second water port communicating the inner chamber with the outer chamber may be designed as follows:

1. When a first end portion of the inner tube is located outside the outer chamber and a second end portion is located inside the outer chamber and sealed independently or together with the end portion of the outer tube corresponding thereto by a mounting plate for mounting the sleeved UV lamps, at least one through-hole may be provided on part of the wall of the inner tube as the second water port, which part being located inside the outer chamber and near the second end portion of the inner tube.

2. When a first end portion of the inner tube is located outside the outer chamber and a second end portion is located inside the outer chamber with the end portion of the outer tube corresponding thereto being sealed by a mounting plate for mounting the sleeved UV lamps, the second end portion of the inner tube, which is totally open or partly sealed, may be used as the second water port; or alternatively, the second end portion of the inner tube is sealed with at least one through-hole provided in the end face thereof as the second water port.

3. When a first end portion and a second end portion of the inner tube are both located outside the outer chamber, at least one through-hole may be provided on part of the wall of the inner tube as the second water port, which part being located inside the outer chamber. In such case, the outer tube is welded on the outer wall of the inner tube, or the outer tube and the outer wall of the inner tube are fixedly or detachably connected by providing respective annular rims or flanges thereon and sealingly connecting them via an annular sealing cover, bolts and the like.

In order to achieve excellent sterilization effect, one of the end portions of the inner tube, which is located inside the outer chamber, may be arranged close to the corresponding end portion of the outer tube, so as to lengthen the path where the fluid is exposed to UV radiation, such that the fluid can receive more UV radiation.

The present invention features the following characteristics:

1. The sleeved UV lamps are arranged in the annular space between the inner tube and the outer tube, thus the intensity of the UV light everywhere in the radiation area is substantially uniform, and the fluid receives a substantially equivalent amount of UV radiation inside the sterilization chamber, thereby achieving substantially the same sterilization effect.

2. At least one water distributor having at least one through-hole is provided in the outer chamber for adjusting the water flow. Said water distributor is a plate with through-hole(s) which enables the water and the sleeved UV lamps to pass through, thereby ensuring that the flow velocity everywhere in the sterilization chamber is uniform and that the fluid everywhere in the sterilization chamber receives the same uniform UV radiation.

3. The UV lamps are arranged between the inner tube and the outer tube, so as to avoid the occurrence of turbulence and improve the sterilization effect.

4. It is possible to provide UV lamps in the inner chamber and/or at both end portions of the wall of the outer tube, so as to increase the intensity of the UV radiation per unit area and the amount of UV radiation that the fluid receives per unit time, thereby treating an increased volume of fluid.

5. The sterilization chamber is modularized, such that two or three or more modules—depending on specific conditions—may be combined for use, if necessary, by connecting with one another via a Swiss patented product, i.e. Straub pipe joint or a flange together with a sealing gasket.

6. The water ports and the sterilization chamber may be sized according to specific conditions, with a corresponding number of UV lamps being provided in the chamber.

7. The water port(s) and the end face(s) outside the sterilization chamber are equipped with a Straub pipe joint or a flange together with a sealing gasket for the purpose of connection, thereby facilitating the disassembly, maintenance and cleaning of the device.

BRIEF DESCRIPTION OF THE DRAWINGS

Hereinafter, the present invention will be described in detail by way of first, second and third embodiments, with reference to the accompanying drawings, in which.

As shown in the figures, an outer tube is designated by 1; a first end portion and a second end portion of the outer tube are respectively designated by 102, 101; an inner tube is designated by 2; a first end portion and a second end portion of the inner tube are respectively designated by 202, 201; an outer chamber is designated by 3; an inner chamber is designated by 4; a first water port, a second water port and a third water port are respectively designated by 6, 15, 5; a water distributor is designated by 7; sleeved UV lamps are designated by 8; a drainage port is designated by 9; a mounting plate for the sleeved UV lamps is designated by 10; flange connecting means are respectively designated by 11, 12, 13; and an end cover is designated by 14.

DETAILED DESCRIPTION OF PREFERRED EMBODIMENT

First Embodiment

Figure 1:
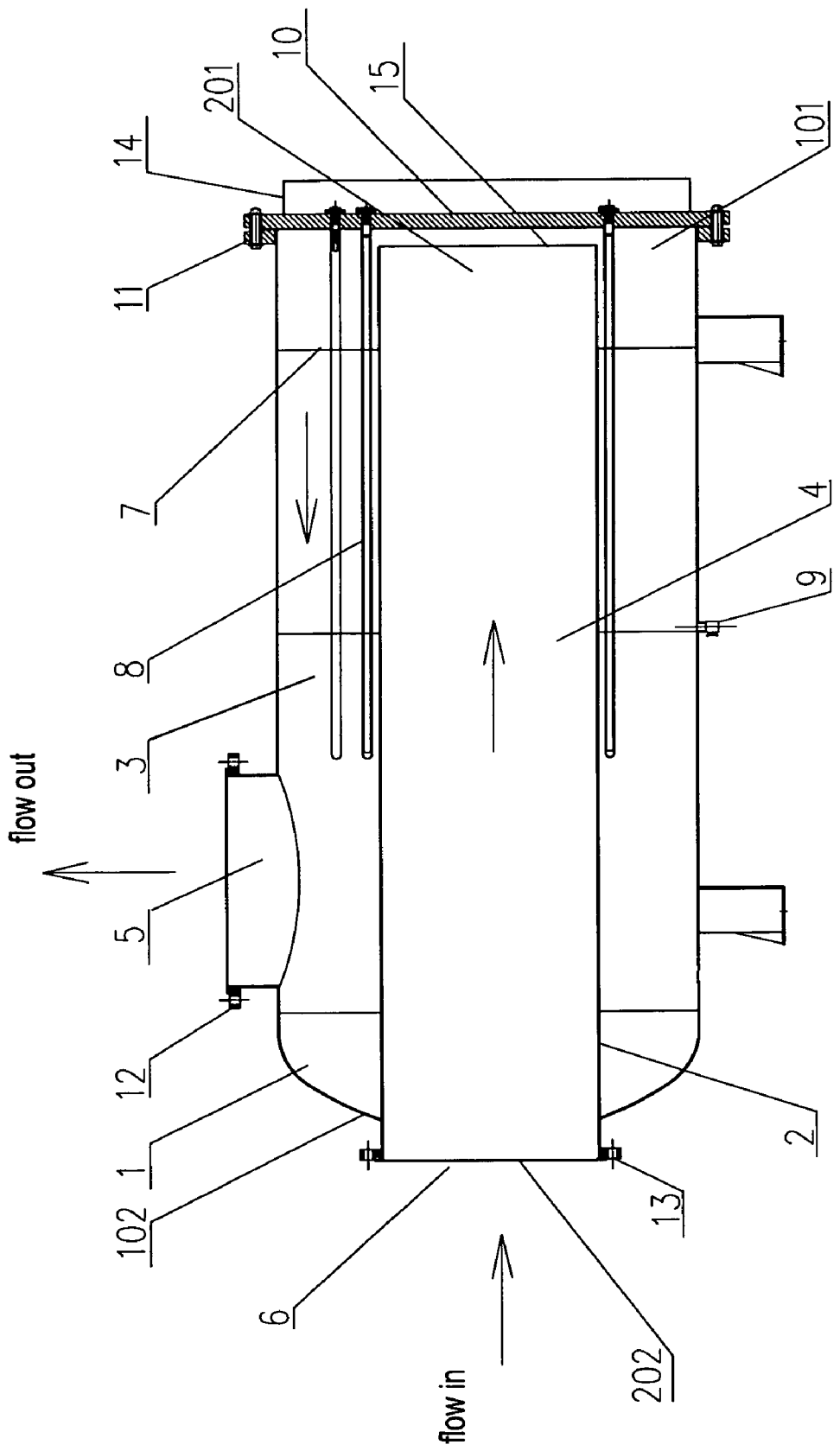
FIG. 1 is a sectional view of the first embodiment according to the present invention.

As shown in FIG. 1, a sterilizer comprises an outer tube 1 and an inner tube 2 with different size, the inner tube being partly surrounded by the outer tube thereby forming an inner chamber and an outer chamber; the inner chamber 4 is the space encircled by the inner tube 2 and the outer chamber 3 is the annular space encircled by the overlapped portions of the inner tube and the outer tube; sleeved UV lamps 8 are arranged in the outer chamber 3; a first end portion 202 of the inner tube 2 is provided with a first water port 6, while a second end portion 201 of the inner tube 2 is located inside the outer chamber 3 and provided with a second water port 15 communicating with the outer chamber 3, in this embodiment, the second end portion 201 of the inner tube 2 is not sealed but used as the second water port 15; a first end portion 102 of the outer tube 1 is sealingly connected with the outer wall of the inner tube 2, while a second end portion 101 of the outer tube 1 is sealed by a mounting plate 10 for the sleeved UV lamps 8; a plurality of mounting holes are provided in the mounting plate 10 for mounting the sleeved UV lamps, the connections between the sleeved UV lamps 8 and the mounting plate 10 are sealed to avoid water leakage; a third water port 5 is provided on the outer tube; at least one water distributor 7 having at least one through-hole is provided in the outer chamber for adjusting the direction and velocity of the water flow; an end cover 14 is provided outside the mounting plate 10; and a drainage port 9 is provided on the wall of the outer chamber for easy access and cleaning. Said distributor is a plate with through-hole(s) which enables the water flow and the sleeved UV lamps to pass through. Since agitation tends to occur when water flows through the distributor, the water will receive more UV radiation so as to achieve a better sterilization effect.

The water ports 5, 6 and the end portion 101 of the outer tube are respectively provided with flanges 11, 12 and 13 for the purpose of connection. In the present embodiment, the water distributor 7 is also used as the support member for the sleeved UV lamps. The water ports 6, 5 are respectively used as the water inlet port and the water outlet port of the sterilizer, or vice versa.

In this embodiment, the outer tube 1 is welded on the outer wall of the inner tube 2, or alternatively, the outer tube and the outer wall of the inner tube are connected by providing respective annular rims or flanges thereon and then sealingly connecting them via an annular sealing cover, bolts and the like.

Therefore, it is possible to sealingly connect the outer tube 1 with the outer wall of the inner tube 2 by an annular sealing cover 103, with the sleeved UV lamps 8 being mounted on the sealing cover 103. Or alternatively, the sleeved UV lamps 8 are provided on both the sealing cover 103 and the mounting plate 10 that is located at the second end portion 101 of the outer tube 1. In other words, the sleeved UV lamps are provided on both end portions of the outer tube simultaneously.

The sleeved UV lamps can also be arranged in the inner chamber 4 for improving the sterilization effect.

Second Embodiment

Figure 2:
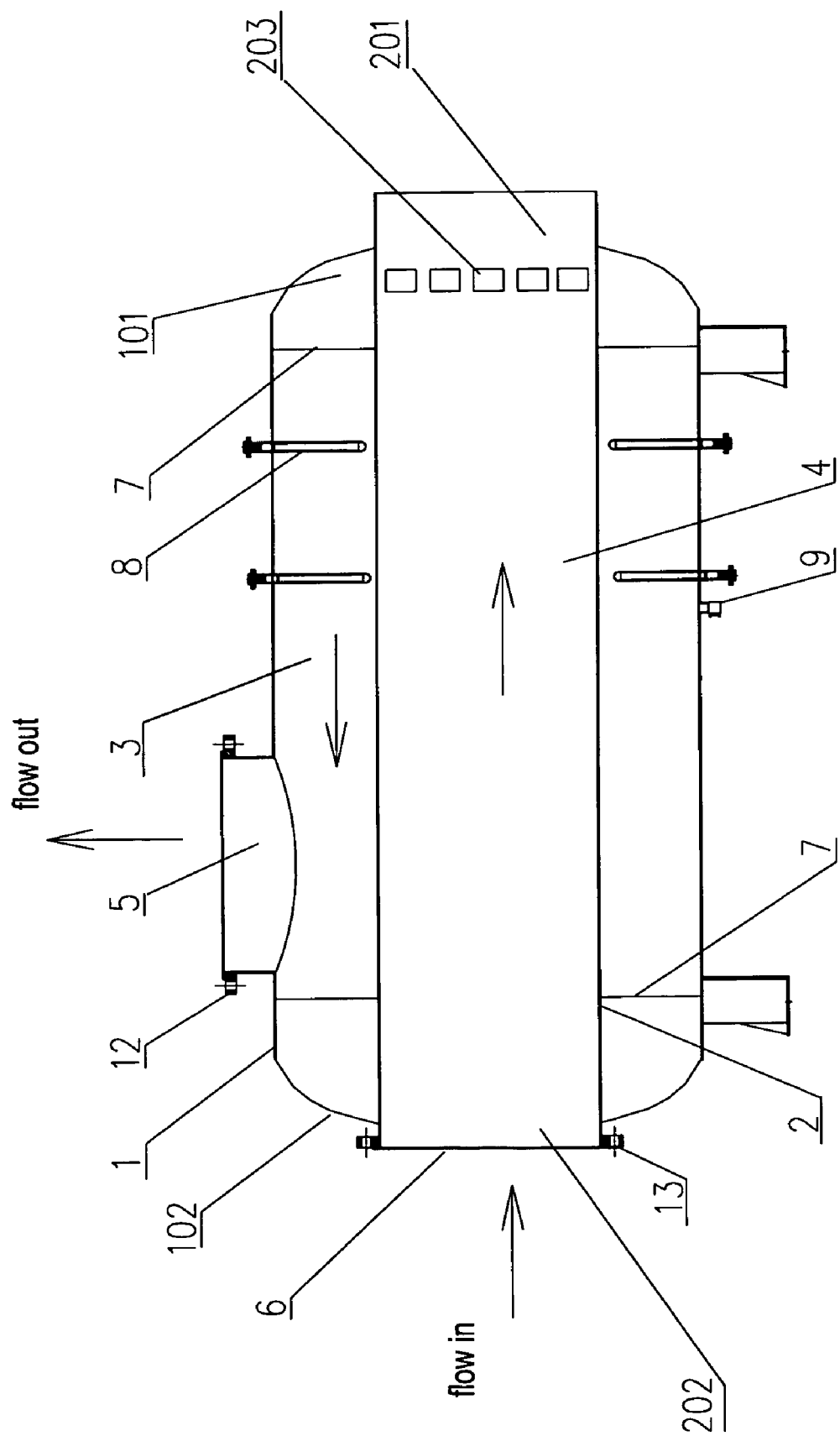
FIG. 2 is a sectional view of the second embodiment according to the present invention.

As shown in FIG. 2, the overall structure of the sterilizer according to the second embodiment is substantially identical with that of the sterilizer in the first embodiment, except that both the first end portion and the second end portion of the inner tube are located outside the outer tube, and the inner tube and the outer tube are sealingly connected. Furthermore, at least one aperture 203 is provided on part of the wall of the inner tube to be used as the water port 15 communicating with the outer chamber 3, which part being located inside the outer chamber 3. Sleeved UV lamps are mounted on the wall of the outer tube.

The sleeved UV lamps may be provided on one of the end portions of the outer tube, or on both the end portions of the outer tube simultaneously, or on the wall and the end portion (s) of the outer tube simultaneously.

Third Embodiment

Figure 3:
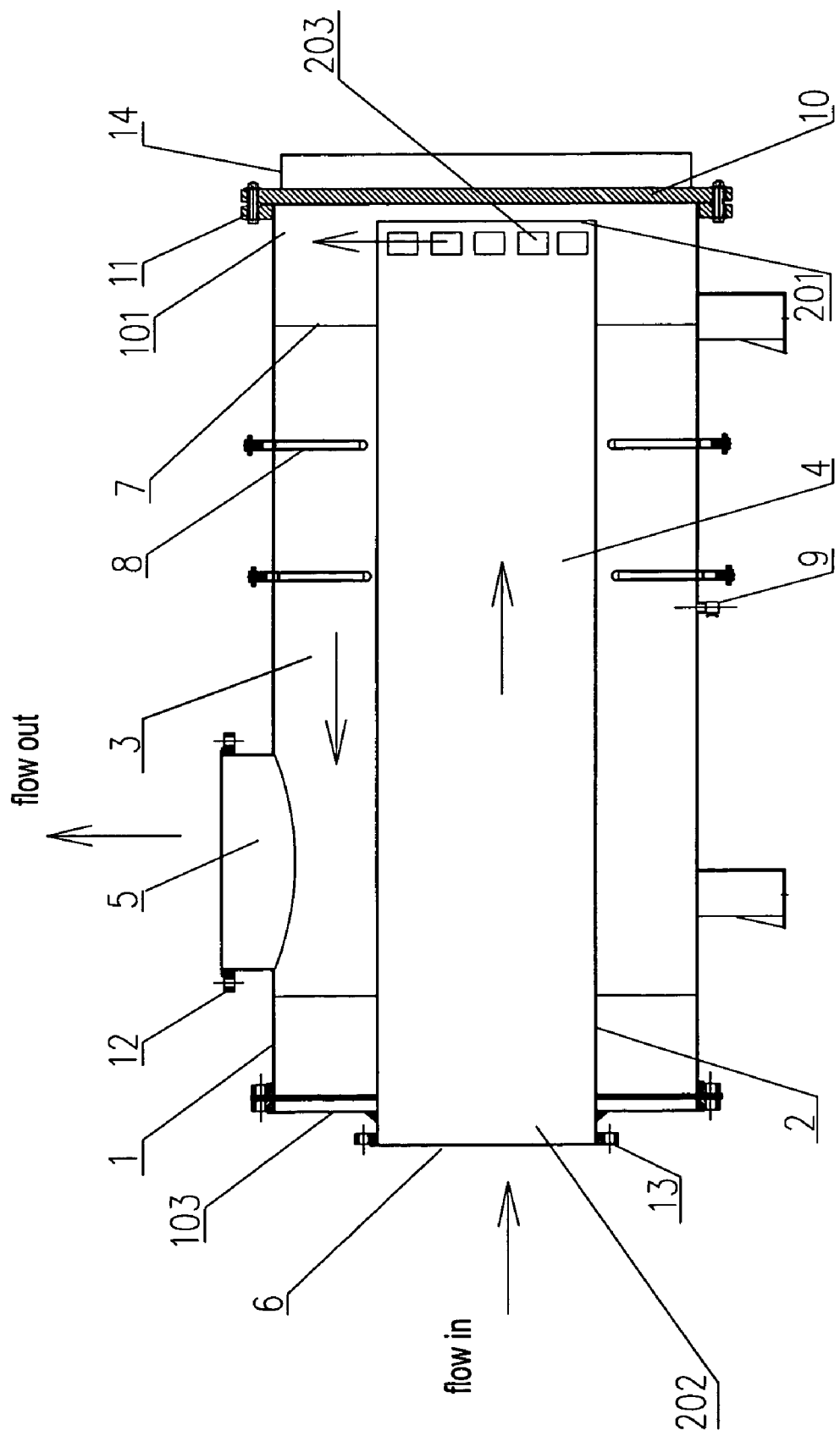
FIG. 3 is a sectional view of the third embodiment according to the present invention.

As shown in FIG. 3, the overall structure of the sterilizer according to the third embodiment is substantially identical with that of the sterilizer in the first embodiment, except that the outer tube and the outer wall of the inner tube are sealingly connected by providing annular rims or flanges thereon and sealingly connecting them via an annular sealing cover, bolts and the like. The end portion 201 of the inner tube is sealed from water, while the wall of the inner tube 2 is provided with at least one aperture 203 to be used as the second water port 15. The sleeved UV lamps 8 are arranged on the wall of the outer tube 1. It is also possible to provide sleeved UV lamps on both end portions of the outer tube 1 simultaneously, so as to increase the intensity of the UV radiation and improve the sterilization effect.

Four Embodiment

Figure 4:
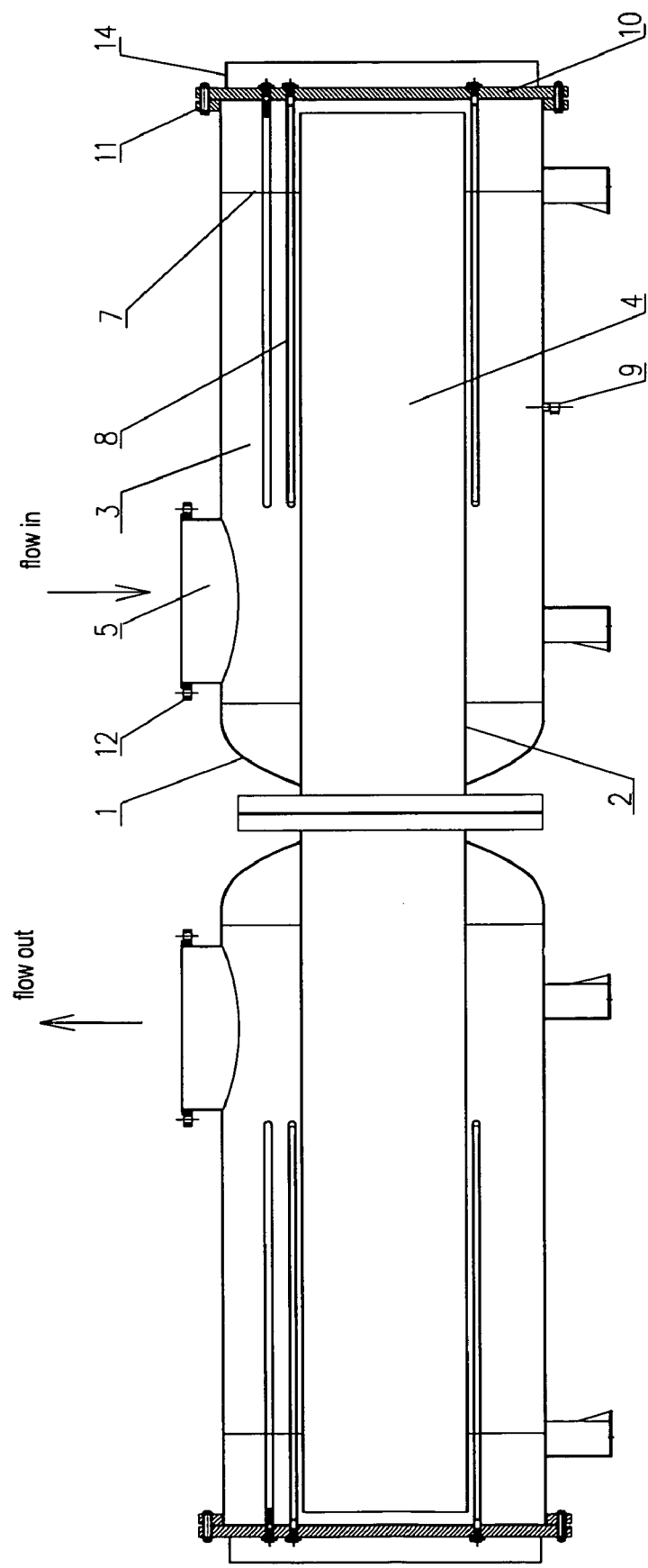
FIG. 4 is a sectional view of the fourth embodiment according to the present invention.

As shown in FIG. 4, the sterilizer in this embodiment is such constructed that two single sterilizers according to the first embodiment are connected in series, thus the path of the water flow is lengthened, increasing the UV radiation that the water receives, or alternatively, increasing the velocity of the fluid flow under the condition that the received UV radiation remains unchanged, such that the sterilizer can treat a larger volume of fluid.

As can be seen from the above-described embodiments, sleeved UV lamps may be disposed on either the end portion (s) or the wall of the outer tube, and they may be additionally provided in the inner chamber to further enhance the sterilization effect. The water port communicating the inner chamber with the outer chamber may be provided in such a manner that one end face of the inner tube is sealed with at least one aperture being provided on the wall thereof, or that the wall of the inner tube is sealed with at least one aperture being provided on one end face thereof.

The single sterilizer in the first to third embodiments may be used as a standard module. In practical applications, two or more modules may be sized and combined for use, so as to improve the sterilization effect and increase the volume of fluid to be treated. Water may flow into the inner tube via a water port of the inner tube for being sterilized and then flow out via a water port of the outer tube, or vice versa.

In the above-described embodiments, the inner and outer tubes are of a cylindrical structure. Of course, they can also take a non-cylindrical shape.

The UV sterilizer according to the present invention may be used for the sterilization of seawater, drinking water, recycled water, treated wastewater and other kinds of water.

Various modifications and improvements can be envisaged by those skilled in the art, without departing from the spirit and gist of the invention.

What is claimed is:

1. A UV sterilizer with a double-chamber structure, characterized in that the sterilizer comprises an outer tube and an inner tube with different size, the inner tube being partly surrounded by the outer tube thereby forming an inner chamber and an outer chamber; the inner chamber is the space encircled by the inner tube and the outer chamber is the annular space encircled by the overlapped portions of the inner tube and the outer tube; at least one sleeved UV lamp is arranged in the outer chamber such that the at least one sleeved UV lamp is closer than the inner tube to an inner wall of the outer tube; a first end portion of the inner tube is located outside the outer chamber and provided with a first water port, a second end portion of the inner tube is located inside the outer chamber and provided with a second water port communicating with the outer chamber; a first end portion of the outer tube is sealingly connected with the outer wall of the inner tube, while a second end portion of the outer tube is sealed; a third water port is provided on the outer tube.

2. The UV sterilizer with a double-chamber structure according to claim 1, characterized in that the second end portion of the outer tube is sealed by a mounting plate for the sleeved UV lamp(s), at least one mounting hole is provided in the mounting plate for mounting the sleeved UV lamp(s); the connection between the sleeved UV lamp(s) and the mounting plate is sealed to avoid water leakage.

3. The UV sterilizer with a double-chamber structure according to claim 1, characterized in that at least one water distributor having at least one through-hole is provided in the outer chamber for adjusting the water flow, thus said water distributor enabling the water and the sleeved UV lamp(s) to pass through.

4. The UV sterilizer with a double-chamber structure according to claim 3, characterized in that the sleeved UV lamp(s) passes through the through-hole(s) in the water distributor, which is used as a support member for the sleeved UV lamp(s).

5. The UV sterilizer with a double-chamber structure according to claim 1, characterized in that said second end portion of the inner tube is sealed by the mounting plate, and at least one through-hole is provided in the wall of the inner tube to be used as the second water port.

6. The UV sterilizer with a double-chamber structure according to claim 1, characterized in that said second end portion of the inner tube is sealed, with at least one through-hole being provided in the end face thereof as the second water port.

7. The UV sterilizer with a double-chamber structure according to claim 1, characterized in that said second end portion of the inner tube is not sealed but used as the second water port.

8. The UV sterilizer with a double-chamber structure according to claim 1, characterized in that the outer tube and the outer wall of the inner tube are sealingly connected by a annular sealing cover, with the sleeved UV lamps being mounted on the sealing cover.

9. The UV sterilizer with a double-chamber structure according to claim 1, characterized in that the sleeved UV lamp(s) is provided on both end portions of the outer chamber simultaneously.

10. The UV sterilizer with a double-chamber structure according to claim 1, characterized in that the sleeved UV lamp(s) is mounted on the wall of the outer chamber.

11. The UV sterilizer with a double-chamber structure according to claim 1, characterized in that said second end portion of the inner tube is located inside the outer chamber and close to the corresponding second end portion of the outer chamber, so as to form a narrow passage for the water flow.

12. The UV sterilizer with a double-chamber structure according to claim 1, characterized in that the UV sterilizer is provided with a drainage port.

13. The UV sterilizer with a double-chamber structure according to claim 1, characterized in that the first water port, the third water port and the second end portion of the outer tube are respectively provided with a flange for the purpose of connection.

14. The UV sterilizer with a double-chamber structure according to claim 1, characterized in that the first water port, the third water port and the second end portion of the outer tube are respectively provided with a Straub pipe joint.

15. The UV sterilizer with a double-chamber structure according to claim 1, characterized in that an end cover is provided on the second end portion of the outer chamber.

16. A UV sterilizer with a double-chamber structure, characterized in that the sterilizer comprises an outer tube and an inner tube with different size, the inner tube being partly surrounded by the outer tube thereby forming an inner chamber and an outer chamber; the inner chamber is the space encircled by the inner tube and the outer chamber is the annular space encircled by the overlapped portions of the inner tube and the outer tube; at least one sleeved UV lamp is arranged in the outer chamber such that the at least one sleeved UV lamp is closer than the inner tube to an inner wall of the outer tube; a first end portion of the inner tube is located outside the outer chamber and provided with a first water port, a second end portion of the inner tube is also located outside the outer chamber and sealed, and a second water port communicating with the outer chamber is provided on part of the wall of the inner tube, which part being located inside the outer chamber; both a first end portion of the outer tube and a second end portion of the outer tube are sealingly connected with the outer wall of the inner tube; a third water port is provided on the outer tube.

\* \* \* \* \*

UNITED STATES PATENT AND TRADEMARK OFFICE
CERTIFICATE OF CORRECTION

PATENT NO. : 7,687,785 B2
APPLICATION NO. : 11/600609
DATED : March 30, 2010
INVENTOR(S) : Jian Chen It is certified that error appears in the above-identified patent and that said Letters Patent is hereby corrected as shown below:

Column 1,
Line 28, "$(n \geqq 1)$" should read --$(n \geq 1)$--

Signed and Sealed this

Eighth Day of June, 2010

David J. Kappos
*Director of the United States Patent and Trademark Office*